United States Patent [19]

Yamada et al.

[11] 4,217,284
[45] Aug. 12, 1980

[54] PROCESS FOR PREPARATION OF OPTICALLY PURE LACTONES FROM MONOESTERS OF CIS-CYCLOPENTENEDIOL

[75] Inventors: Shun-ichi Yamada, Chofu; Shiro Terashima, Tokyo; Masahiko Nagakura, Sayama; Munehiko Nara, Tokyo, all of Japan

[73] Assignee: Kowa Company Ltd., Nagoya, Japan

[21] Appl. No.: 920,833

[22] Filed: Jun. 30, 1978

Related U.S. Application Data

[62] Division of Ser. No. 839,356, Oct. 4, 1977, Pat. No. 4,170,596.

[30] Foreign Application Priority Data

Oct. 5, 1976 [JP] Japan ............................ 51-119745
Oct. 5, 1976 [JP] Japan ............................ 51-119746
Oct. 5, 1976 [JP] Japan ............................ 51-119747

[51] Int. Cl.$^2$ ........................................... C07D 307/93
[52] U.S. Cl. ............................................. 260/343.3 P
[58] Field of Search ................... 260/343.3 R, 343.3 P

[56] References Cited

U.S. PATENT DOCUMENTS

| | | | |
|---|---|---|---|
| 3,887,606 | 6/1975 | Phillipps et al. ..................... | 560/38 |
| 3,904,648 | 9/1975 | Kelly ................................ | 260/514 D |
| 3,970,673 | 7/1976 | Kondo et al. ..................... | 260/343.3 R |
| 3,976,680 | 8/1976 | Clark et al. ........................ | 560/38 |
| 4,012,429 | 3/1977 | Sakai et al. ...................... | 260/343.3 P |
| 4,064,351 | 12/1977 | Sakai et al. ..................... | 260/343.3 R |

OTHER PUBLICATIONS

Corey et al., Tetrahedron Letters, No. 4, pp. 311-313, 1970.
Corey et al., Tetrahedron Letters, No. 28, pp. 2439-2440, 1974.
Corey et al., Jour. of Amer. Chem. Soc., 91:20, Sep. 1969, pp. 5675-5677.
Kondo et al., Angnew. Chem., Internat. Edit., vol. 14, 1975, No. 2, p. 103.
Partridge et al., Jour. of the Amer. Chem. Soc., 95:21, Oct. 17, 1973.
Mitra, The Synthesis of Prostaglandins, 1977, p. 243, John Wiley & Sons, New York.
Takno et al., Journal of the Chemical Society Chemical Communications, Jun. 1976, pp. 189-190.
Reese, Protective Groups in Organic Chem., Edited by McOmie, 1973, Plenum Press.

Primary Examiner—Natalie Trousof
Assistant Examiner—Jane T. Fan
Attorney, Agent, or Firm—Sherman & Shalloway

[57] ABSTRACT

A novel monoester of cis-cyclopentenediol of the following formula

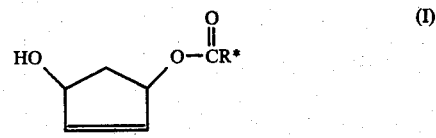

wherein

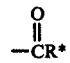

is an optically active acyl moiety. The monoester can be prepared by reacting cis-2-cyclopentene-1,4-diol with an optically active carboxylic acid of the following formula

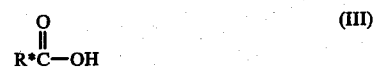

wherein

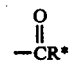

is the same as defined above, or its reactive derivative, and separating the resulting reaction product into the two individual diastereomers. Lactones can be prepared from the monoesters selectively and with commercial advantage.

10 Claims, No Drawings

PROCESS FOR PREPARATION OF OPTICALLY PURE LACTONES FROM MONOESTERS OF CIS-CYCLOPENTENEDIOL

This is a division, of application Ser. No. 839,356, filed Oct. 4, 1977 now U.S. Pat. No. 4,170,596, Oct. 9, 1979.

This invention relates to a process for preparing lactones having a desired absolute configuration which are important intermediates for the production of pharmacologically useful prostaglandins; novel monoesters of cis-cyclopentenediol; and a process for producing these monoesters.

More specifically, the invention relates to novel monoesters of cis-cyclopentenediol of the following formula

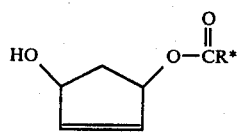 (I)

wherein

is an optically active acyl moiety, a process for preparation thereof; and a process for preparing lactones of the following formula

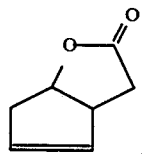 (IV)

from the monoesters of formula (I) selectively and with commercial advantage.

The novel monoester of cis-cyclopentenediol of formula (I) may contain two forms of diastereomers of the following formulae (I-1) and (I-2) which are monoesters of 1(R)4(S)- and 1(S)4(R)-4-hydroxy-2-cyclopentenols:

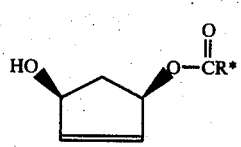 (I-1)

wherein

is an optically active acyl moiety

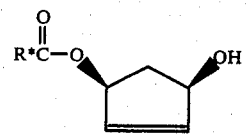 (I-2)

wherein

is the same as defined above.

The lactones of formula (IV) may have two forms of enantiomers, (+)-1(R)5(S)- and (−)-1(S)5(R)2-oxabicyclo[3,3,0]oct-6-en-3-one, of the following formulas (IV-1) and (IV-2):

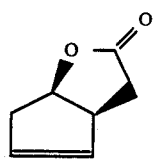 (IV-1)

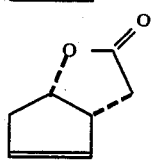 (IV-2)

Some prior suggestions are known for the production of compounds of formula (IV).

For example, Angew. Chem. Internat. Edit., 14, 103 (1975) states that dl-2-oxa-bicyclo[3,3,0]oct-6-en-3-one was obtained in a yield of 85% in accordance with the following reaction scheme:

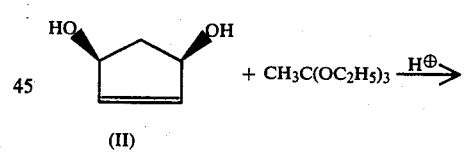

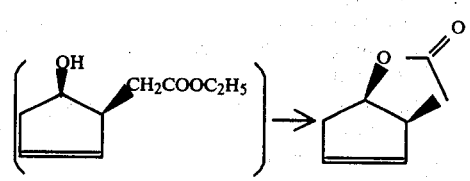

However, the resulting product is a 1:1 mixture of the two individual enantiomers of formulae (IV-1) and (IV-2). No separation was performed in the procedure disclosed in this reference, and therefore, the above yield is that of the mixture. In order to obtain an optically pure product, an enantiomer having the desired absolute configuration is taken out by optical resolution, and the product having the opposite configuration must be discarded.

J. Amer. Chem. Soc., 95 7171 (1973) discloses the preparation of (−)-1(S)5(R)-2-oxa-bicyclo[3,3,0]oct-6-en-3-one (IV-2) by the reaction schematically shown as follows:

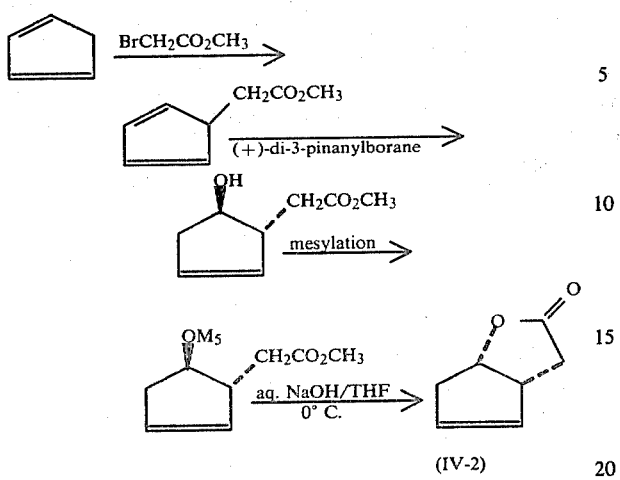

If it is desired to obtain (+)-1(R)5(S)-2-oxa-bicyclo[3,3,0]oct-6-en-3-one by the above reaction, (−)-di-3-pinanylborane is used instead of the (+)-di-3-pinanylborane. However, the use of these pinanylboranes which are difficult to synthesize and expensive is essential in this method, and it is quite unsuitable for commercial performance.

It is well known that pharmacologically useful prostaglandins can be prepared through very few process steps from the lactones of formulae (IV-1) and (IV-2) (see, for example, Tetrahedron Letters, 1970, 311, and Tetrahedron Letters, 1974, 2439).

It is known on the other hand that the configuration of a prostaglandin has closely to do with its pharmacological actions. In order therefore to obtain the desired prostaglandins with commercial advantage, stereoisomers convertible to prostaglandins having the desired configuration must be obtained in as high purity as possible and in the best possible yields in any of their synthetic pathways.

In the first-cited reference, the compounds of formulae (IV-1) and (IV-2) must be separated, and one of the desired stereoisomers is utilized, and therefore, the yield of the desired prostaglandin is reduced to half. The second suggestion cited above cannot avoid the use of expensive reagents which are difficult to synthesize, and is quite unsuitable for commercial performance.

The present inventors made extensive ingestigation in order to overcome these disadvantages and to develop a new synthetic route for producing optically active lactones of formulae (IV-1) and (IV-2) having the desired configuration at low costs and in high yields.

These investigations led to the discovery that novel monoesters of cis-cyclopentenediol of formula (I) can be prepared easily in good yields, and one of the optically active lactones of formulae (IV-1) and (IV-2) having the desired configuration can be prepared easily in good yields from the two diastereomers of formulae (I-1) and (I-2) separated from the novel monoesters. While in the production of optically active lactones having the desired absolute configuration by the prior suggestions, one of the two stereoisomers cannot be utilized, or the use of reagents unsuitable for commercial operation is required, the use of the novel monoesters of this invention makes it possible to produce lactones having the desired absolute configuration through new synthetic pathway in high yields by a simple operation with commercial advantage.

Accordingly, it is an object of this invention to provide novel monoesters of cis-cyclopentenediol, and a process for preparation thereof.

Another object of this invention is to provide a process for preparing lactones having the desired absolute configuration, which are important intermediates for the preparation of pharmacologically useful prostaglandins, selectively with commercial advantage.

The above and other objects and advantages of this invention will become more apparent from the following description.

The novel monoesters of cis-cyclopentenediol of the formula

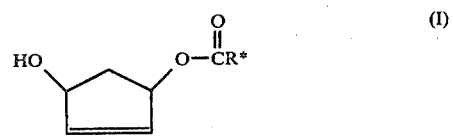

wherein

is an optically active acyl moiety, includes two diastereomers, novel monoesters of 1(R)4(S)-4-hydroxy-2-cyclopentenol of the following formula (I-1) and novel monoesters of 1(S)4(R)-4-hydroxy-2-cyclopentenol of the following formula (I-2).

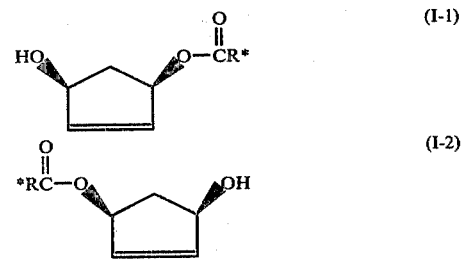

wherein

is the same as defined above.

Preferably, the optically active acyl moiety is an acyl moiety derived from an optically active carboxylic acid in which excepting one carboxyl group, all functional groups that may exist are protected. Especially preferably, the acyl moiety is derived from an optically active carboxylic acid which is selected from the group consisting of optically active amino acids whose functional groups excepting one carboxyl group (for example, the amino group and other functional groups which may exist) are protected, optically active hydroxy-carboxylic acids whose functional groups excepting one carboxyl group (for example, the hydroxyl group and other functional groups which may exist) are protected, and optically active carboxylic acids containing no functional group excepting one carboxyl group.

Examples of the optically active amino acids are optically active neutral amino acids whose amino groups are protected, optically active basic amino groups whose amino groups and other basic groups are protected, optically active acidic amino acids whose amino groups and carboxyl groups excepting one carboxyl group are protected, and optically active hydroxy-containing amino acids whose amino and hydroxyl groups are protected. The use of optically active neutral amino acids whose amino groups are protected is most preferred. Especially amino-protected optically active neutral α-amino acids are preferred. Examples of the optically active neutral amino acids are alanine, valine, norvaline, isoleucine, leucine, norleucine, proline, phenylalanine, phenylglycine, glutamine, asparagine, and methionine.

Examples of the optically active basic amino acids are histidine, arginine, ornithine, and lysine. Examples of the optically active acidic amino acids are glutamic acid and aspartic acid. Examples of the optically active hydroxy-containing amino acids are serine, threonine, tyrosine, and hydroxyproline.

is an optically active acyl moiety, or a reactive derivative thereof, and separating the resulting reaction product into the two individual diastereomers.

The monoester of 1(R)4(S)-4-hydroxy-2-cyclopentenol of formula (I-1) and the monoester of 1(S)4(R)-4-hydroxy-2-cyclopentenol of formula (I-2) can also be prepared by the following process (A') which comprises protecting one hydroxyl group of cis-2-cyclopentene-1,4-diol of formula (II) above with an acid-sensitive protective group, then reacting it with the optically active carboxylic acid of formula (III) above or its reactive derivative, treating the resulting reaction product with an acid to remove the protective group, and then separating the product into the two individual diastereomers.

The processes (A) and (A') can be schematically shown below.

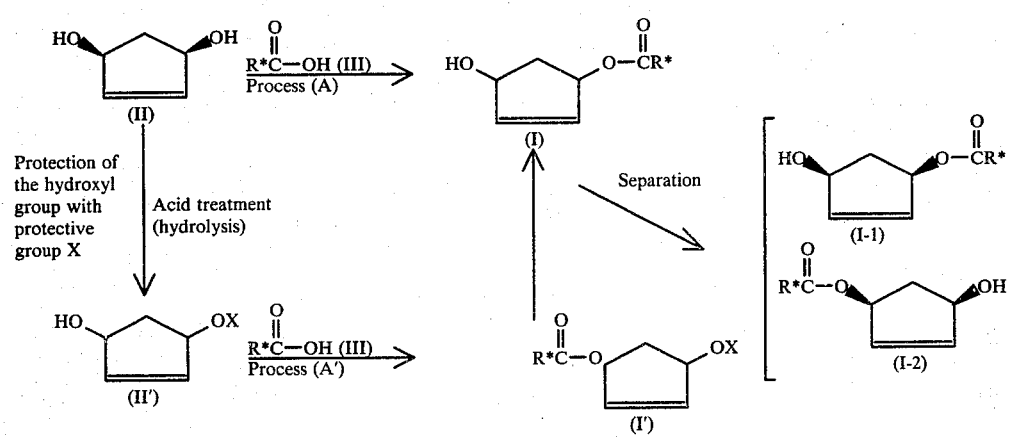

Examples of the optically active hydroxy-carboxylic acid are tartaric acid, malic acid, mandelic acid, lactic acid, glyceric acid, quinic acid, 3-hydroxybutyric acid, and p-hydroxyphenyl-lactic acid.

Menthoxyacetic acid and hydratropic acid are examples of the optically active carboxylic acid having no functional group excepting one carboxyl group.

The monoester of 1(R)4(S)-4-hydroxy-2-cyclopentenol of formula (I-1) and the monoester of 1(S)4(R)-4-hydroxy-2-cyclopentenol of formula (I-2) can be prepared by the following process (A) which comprises reacting cis-2-cyclopentene-1,4-diol of the following formula

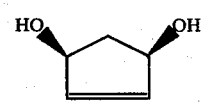

with an optically active carboxylic acid of the following formula

wherein

The diester of the following formula

which may be formed as a by-product in process (A) can be easily converted to the cis-2-cyclopentene-1,4-diol of formula (II) by hydrolysis with alkalies, and simultaneously, optically active carboxylic acid of formula (III) can be recovered without racemisation. In process (A'), too, the compound of the formula which may be formed as a by-product can be easily converted to the compound of formula (II) by hydrolysis with acids. Since products other than the compounds of formulae (I-1) and (I-2) can be converted to the starting compounds, the process of this invention can afford the novel monoesters of 1(R)4(S)-4-hydroxy-2-cyclopentenol and 1(S)4(R)-4-hydroxy-2-cyclopentenol with commercial advantage.

The optically active carboxylic acid of formula (III) may be an optically active carboxylic acid in which excepting one carboxyl group, all functional groups that may exist are protected. Examples of preferred carboxylic acids are optically active amino acids whose functional groups excepting one carboxyl groups (for example, the amino group and other functional groups which may exist) are protected, optically active hydroxy-carboxylic acids whose functional groups excepting one carboxyl group (for example, the hydroxyl group and other functional groups which may exist) are protected, and optically active carboxylic acids containing no functional group excepting one carboxyl group.

Specific examples of these optically active carboxylic acid are the same as those exemplified hereinabove with regard to the optically active acyl moiety in the compounds of formulae (I-1) and (I-2).

Examples of the reactive derivatives of the optically active carboxylic acids of formula (III) are their halides, anhydrides and active esters.

Examples of the protective group for amino are sulfonyl groups such as tosyl, mesyl or brosyl; acyl groups such as acetyl, propionyl, benzoyl, p-nitrobenzoyl or phthaloyl; alkyloxycarbonyl groups such as ethyloxycarbonyl, tert.butyloxycarbonyl or tert.lamyloxycarbonyl; cycloalkyloxycarbonyl groups such as cyclohexyloxycarbonyl; aralkyloxycarbonyl groups such as benzyloxycarbonyl or p-methoxybenzyloxycarbonyl; and an o-nitrosulfenyl group. Examples of the protective group for hydroxyl are alkyl groups and the acyl groups given above.

Sulfonyl groups such as tosyl or mesyl are especially preferred as protective groups for amino.

According to process (A), the monoester of cis-cyclopentenediol of formula (I) can be produced by reacting the diol of formula (II) with the optically active carboxylic acid of formula (III) or its reactive derivative in an organic solvent in the presence or absence of a base. The carboxylic acid of formula (III) or its reactive derivative is used preferably in an amount of about one mole per mole of the diol of formula (II).

Examples of the base include tertiary amines such as triethylamine, dimethylaniline or pyridine; quaternary ammonium salts such as a trimethylbenzyl ammonium salt; and inorganic bases such as alkali carbonates and alkali hydroxides.

Examples of the organic solvents are hydrocarbons such as benzene, toluene, xylene, cyclohexane, petroleum ether, and petroleum benzin; ethers such as diethyl ether, methyl ethyl ether, dioxane and tetrahydrofuran; ketones such as acetone and methyl ethyl ketone; and basic solvents such as pyridine.

The reaction ends in about 5 to 20 hours at room temperature, and heating is not particularly required. If desired, however, the reaction may be accelerated by heating. Thus, the reaction temperature may be from room temperature to about 80° C. The reaction product can be separated into the two individual diastereomers of formulae (I-1) and (I-2) by fractional recrystallization or chromatography. At this time, it is desirable to perform the separating operation after removing the by-product diester by such means as chromatography or fractional distillation. The by-product diester can be easily converted to the diol of formula (II) by alkali hydrolysis as stated hereinabove. Examples of solvents which can be used for the fractional recrystallization are diethyl ether, tetrahydrofuran, alcohols, water, benzene, toluene, chloroform, carbon tetrachloride, petroleum ether, hexane and acetone. Types of chromatography which can be used are, for example, column chromatography, and preparative thin-layer chromatography. For example, the chromatography can be performed over silica gel or alumina using an eluent which may be those exemplified above as recrystallization solvents.

According to process (A'), one hydroxyl group of the diol of formula (II) is protected with a protective group X to form the monoether of formula (II') which is then reacted with the optically active carboxylic acid of formula (III) or its reactive derivative in the same way as in process (A) to form the compound of formula (I'). The carboxylic acid of formula (III) may be used in an amount of at least one mole per mole of the monoether (II'). The protective group X includes, for example, tetrahydropyranyl, trimethylsilyl, tri-n-butyltin, and 1-methoxy-4-tetrahydropyranyl. When tetrahydropyranyl is used as the protective group, the diol of formula (II) and dihydropyran are used in substantially equimolar proportions, and reacted at room temperature for about 30 minutes to about 20 hours in the same organic solvents as described with regard to process (A) except basic solvents to form the monoether of formula (II'). The by-product diether in the resulting reaction product can be removed by, for example, chromatography or distillation. The by-product diether can be easily converted to the starting diol of formula (II) by acid hydrolysis as stated hereinabove. In the present invention, the reaction product may be reacted with the optically active carboxylic acid of formula (III) or its reactive derivative in the same way as described hereinabove with regard to process (A) without prior removal of the by-product diether. Acid treatment (e.g., acetic acid treatment) of the resulting compound of formula (I') easily causes the removal of the protective group X to form the monoester of cis-cyclopentenediol of formula (I) which can be separated into the two individual diastereomers of formulae (I-1) and (I-2) in the same way as described hereinabove with regard to process (A).

According to the invention, the (+)-1(R)5(S)-2-oxa-bicyclo[3,3,0]oct-6-en-3-one of formula (IV-1) can be produced from any of the monoesters of formulae (I-1) and (I-2) [process (B) and process (C') to be described hereinbelow]. Likewise, the (−)-1(S)5(R)-2-oxa-bicyclo[3,3,0]oct-6-en-3-one can be prepared from any of the monoesters [process (C) and process (B') to be described hereinbelow.

Hence, according to the present invention, lactones having the desired absolute configuration which are important intermediates for the production of optically active prostaglandins can be produced selectively in high yields with commercial advantage.

For easy understanding, processes (B), (B'), (C) and (C') are schematicaly shown below.

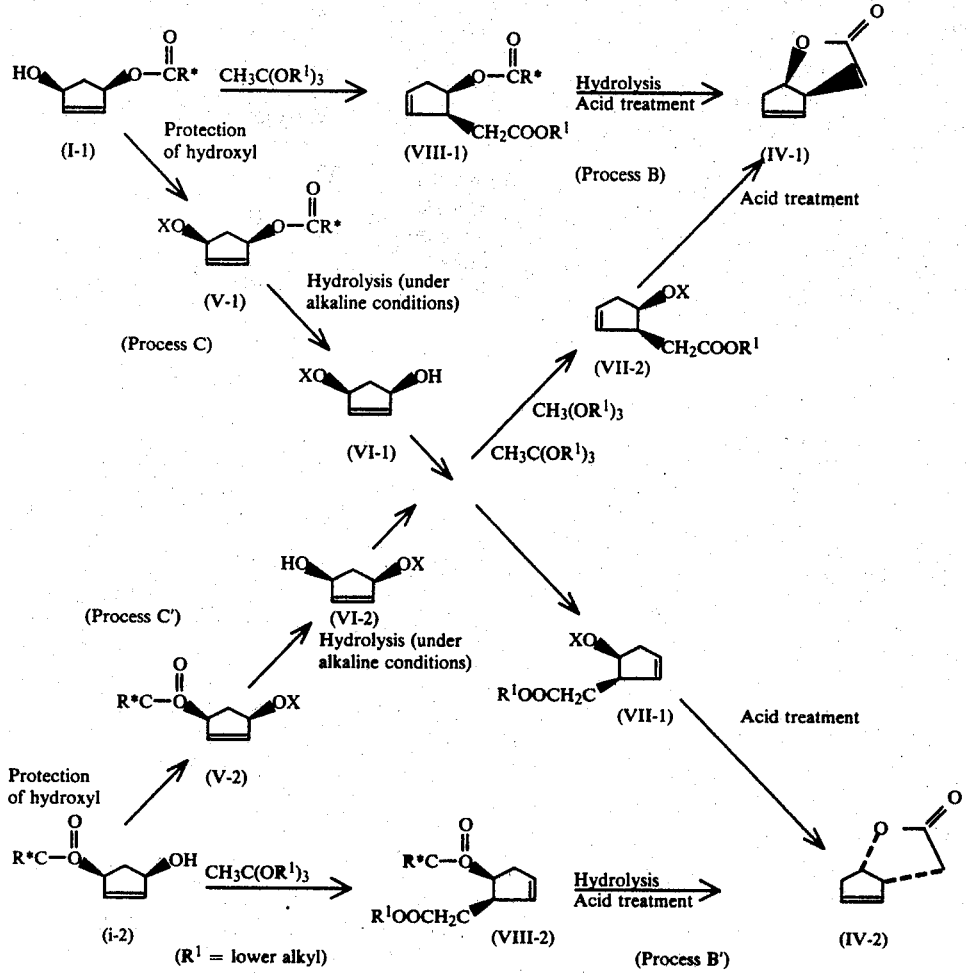

As schematically shown above, according to processes (B) and (B'), a lactone of the following formula

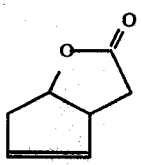 (IV)

can be prepared by reacting a monoester of cis-cyclopentenediol of the following formula

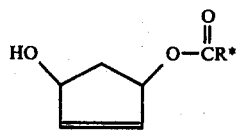 (I)

wherein

is an optically active acyl moiety, with a trialkyl orthoacetate, hydrolyzing the reaction product, and then treating the hydrolyzate with an acid.

According to process (B), the monoester of formula (I) is a monoester of 1(R)4(S)-4-hydroxy-2-cyclopentenol of the following formula

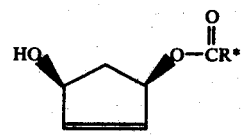 (I-1)

wherein

is the same as defined hereinabove, and (+)-1(R)5(S)-2-oxa-bicyclo[3,3,0]oct-6-en-3-one of the following formula

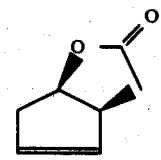 (IV-1)

is obtained. According to process (B'), the monoester of formula (I) is a monoester of 1(S)4(R)-4-hydroxy-2-cyclopentenol of the following formula

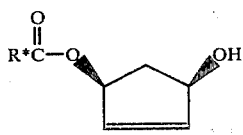
(I-2)

wherein

is the same as defined hereinabove, and (−)-1(S)5(R)-2-oxa-bicyclo[3,3,0]oct-6-en-3-one of the following formula

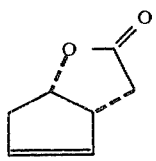
(IV-2)

can be obtained.

The reaction of the monoester of cis-cyclopentenediol of formula (I) in the form of (I-1) or (I-2) with the trialkyl orthoacetate can be easily performed by contacting the monoester and trialkyl orthoacetate of the formula $CH_3C(OR')_3$ in which R' is lower alkyl in the presence or absence of an acid. The contacting causes condensation, followed by Claisen rearrangement to form a compound of the following formula

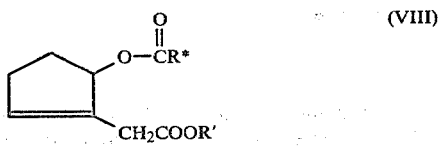
(VIII)

wherein

and R' are the same as defined hereinabove. The compound of formula (VIII-1) is produced from the monoester of formula (I-1), and the compound of formula (VIII-2) from the monoester of formula (I-2). Preferably, the reaction of forming the compound of formula (VIII) is carried out using an excess of the trialkyl orthoacetate (e.g., triethyl orthoacetate) to cause it to act concurrently as a solvent. Needless to say, other suitable solvents, such as dimethyl formamide and dimethyl sulfoxide, may be used in this reaction. Examples of the acid which may be copresent during the reaction are organic weak acids such as propionic acid, hydroquinone, and phenol. The reaction can be performed at a temperature of, say, about 100 to about 300° C. for a period of, say, about 1 to about 20 hours. The resulting compound of formula (VIII) can be used in the subsequent reaction without isolation. If desired, the subsequent reaction may be carried out using the isolated, or isolated and purified, reaction product. Hydrolysis of the resulting reaction product can be carried out in the presence of an alkali in a solvent. Examples of the alkali are alkali hydroxides such as potassium hydroxide and sodium hydroxide, and organic amines such as triethylamines. Usable solvents include, for example, water, and organic solvents, for example, lower alcohols such as methanol, ethanol or propanol, acetone, and tetrahydrofuran. The organic solvents may be used alone or as a mixture with water. The reaction can be performed at room temperature for several hours to several days. The reaction can be accelerated by heating to about 100° C., for example.

Treatment of the hydrolyzed product of the compound of formula (VIII), where

and R' are hydrogen atoms, with an acid affords the desired compound of formula (IV). The compound of formula (IV-1) can be obtained from the compound of formula (VIII-1), and the compound of formula (IV-2), from the compound of (VIII-2). The acid includes, for example, mineral acids such as hydrochloric acid and sulfuric acid, and organic acids such as p-toluenesulfonic acid and acetic acid. The reaction proceeds advantageously in a solvent. Examples of usable solvents are halogenated hydrocarbons, ethers, esters, and ketones in addition to those specifically exemplified hereinabove with regard to the hydrolysis reaction. The reaction proceeds at room temperature over the course of several hours to several days, and can be accelerated by heating. Separation and purification of the product by a usual procedure such as chromatography, distillation or recrystallization afford the desired compound of formula (IV) which has an optical purity of 100%.

According to processes (C) and (C') shown in the above scheme, a lactone of the following formula

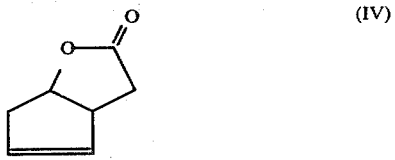
(IV)

can be prepared by protecting the hydroxyl group of a monoester of cis-cyclopentenediol of the following formula

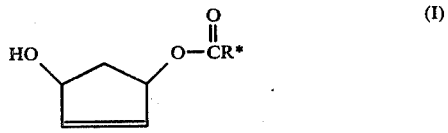
(I)

wherein

is an optically active acyl moiety, with an acid-sensitive protective group X, then hydrolyzing the compound with alkalies to form a compound of the following formula

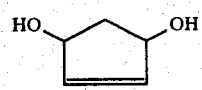 (VI)

reacting the compound with a trialkyl orthoacetate, if desired hydrolyzing the reaction product, and treating the product with an acid.

According to process (C), the monoester of formula (I) is a monoester of 1(R)4(S)-4-hydroxy-2-cyclopentenol expressed by the following formula

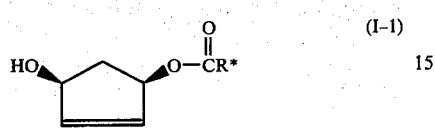 (I-1)

and (−)-1(S)5(R)-2-oxa-bicyclo[3,3,0]oct-6-en-3-one of the following formula

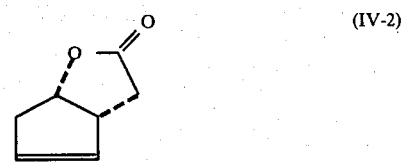 (IV-2)

can be obtained. According to process (C'), the monoester of formula (I) is a monoester of 1(S)4(R)-4-hydroxy-2-cyclopentenol of the following formula

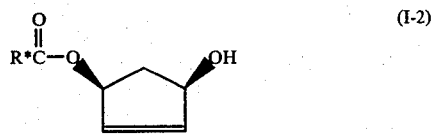 (I-2)

wherein

−CR* is the same as defined above, and (+)-1(R)5(S)-2-oxa-bicyclo[3,3,0]oct-6-en-3-one of the following formula

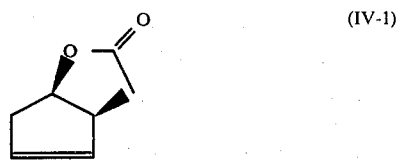 (IV-1)

can be obtained.

The acid-sensitive protective group X used in processes (C) and (C') may be those exemplified above for use in protecting one hydroxyl group of the diol of formula (II). For example, when a tetrahydropyranyl group is used as the protective group X, the monoester of cis-cyclopentenediol of formula (I) and dihydropyran are used in substantially equimolar proportions and can be reacted in an organic solvent at room temperature for about 30 minutes to about 20 hours. If desired, the reaction can be performed under heat. Temperatures of from room temperature to about 80° C. can usually be used for the reaction. Preferably, the reaction is carried out in the copresence of a small amount of an acid such as p-toluenesulfonic acid to accelerate the reaction. Examples of the organic solvent include hydrocarbons such as benzene, toluene, xylene, cyclohexane, petroleum ether and petroleum benzin; halogenated hydrocarbons such as methyl chloride, methylene chloride, chloroform, carbon tetrachloride, ethyl chloride and ethylene chloride; ethers such as diethyl ether, methyl ethyl ether, dioxane and tetrahydrofuran; ketones such as acetone and methyl ethyl ketone; and esters such as methyl acetate, ethyl acetate, ethyl propionate and ethyl butyrate.

Hydrolysis of the resulting compound of the formula

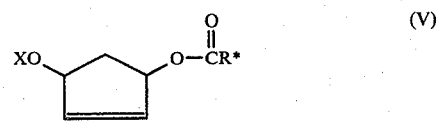 (V)

wherein

−CR* is the same as defined hereinabove, and X is an acid-sensitive protective group, with alkalies can afford a compound of the following formula

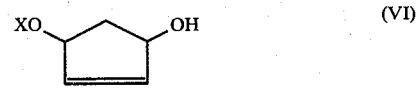 (VI)

In the above reaction scheme, the compound of formula (VI-1) is formed from the compound of formula (V-1), and the compound of formula (VI-2), from the compound of formula (V-2). The alkalies may be the same as those exemplified above for use in hydrolyzing the compound of formula (VIII-1) in process (B). The reaction can be performed in an aqueous medium. The aqueous medium may be the same solvents as exemplified above for use in hydrolyzing the compound of formula (VIII-1). Since the reaction proceeds at room temperature, heating is not particularly required. However, the reaction can be accelerated by heating. Usually, temperatures of from room temperature to about 100° C. can be used. The reaction time is, for example, from several hours to several days.

Claisen rearrangement is induced by reacting the resulting compound of formula (VI) with the same trialkyl orthoacetate as mentioned above with regard to processes (B) and (B') to afford a compound of the following formula

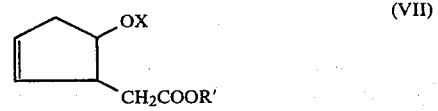 (VII)

wherein X and R' are the same as defined above. The compound of formula (VII-1) can be formed from the compound of formula (VI-1), and the compound of formula (VII-2), from the compound of formula (VI-2). The above reaction can be easily carried out by contacting the compound of formula (VI) with the trialkyl orthoacetate in the presence or absence of acids as described above with regard to the reaction of forming the compound of formula (VIII) from the compound of formula (I) by the processes (B) and (B'). The acid which may be used includes the same weak acids as described above with regard to the processes (B) and (B'). The reaction can be performed at about 100° to 300° C. for about 1 to 20 hours.

Treatment of the resulting reaction product with an acid can afford the compound of formula (IV). The compound of formula (IV-2) can be obtained from the compound of formula (VII-1), and the compound of formula (IV-1), from the compound of formula (VII-2). The acid used for this acid treatment may be the same as those exemplified above with regard to the acid treatment after the hydrolysis of the compound of formula (VIII) in processes (B) and (B'), and the same reaction conditions can be used. The usable solvents include alcohols in addition to those exemplified above with regard to processes (B) and (B'). Prior to the above reaction, the compound of formula (VII) may be hydrolyzed under alkaline conditions to cleave the ester group as described hereinabove with regard to the reaction of forming the compound of formula (IV) from the compound of formula (VIII) in the processes (B) and (B'). The hydrolysis reaction can be performed in the same way as described with regard to processes (B) and (B'). The resulting compound of formula (IV) can be separated and purified in the same way as described hereinabove with regard to the processes (B) and (B').

Thus, according to this invention, $(-)$-1(S)5(R)2-oxa-bicyclo[3,3,0]oct-6-en-3-one of formula (IV-2) can be obtained from any of the compounds of formulae (I-1) and (I-2) by the processes (C) and (B'). Furthermore, $(+)$-1(R)5(S)-2-oxa-bicyclo[3,3,0]oct-6-en-3-one of formula (IV-1) can be obtained from any of the compounds of formulae (I-1) and (I-2) by processes (B) and (C').

The use of the novel monoester of cis-cyclopentenediol of this invention can get over the disadvantages of the conventional processes in which only one of the isomers can be used, and makes it possible to produce the lactone of formula (IV) having the desired absolute configuration from any of the isomers of formulae (I-1) and (I-2). Hence, the present invention can provide a process for producing lactones of formula (IV) with marked commercial advantage, in which the two isomers of the monoester of formula (I) can be entirely utilized. Moreover, the present invention makes it possible to easily produce the novel monoesters having the aforesaid advantages by using the meso-form of formula (II) which has hitherto not been used as a material for the synthesis of optically active products, as a starting material and the cheap and readily available optically active carboxylic acids described above as a reagent.

The following Examples illustrate the present invention in more detail.

EXAMPLE 1

A solution of 10.0 g of N-mesyl-L-phenylalanyl chloride in 30 ml of tetrahydrofuran was added dropwise to a solution of 3.80 g of cis-2-cyclopentene-1,4-diol in 150 ml of pyridine over a period of one hour with stirring. The resulting mixture was further stirred at room temperature for 15 hours. After the reaction, the solvent was evaporated under reduced pressure. The residue was dissolved in ethyl acetate, washed with water and dried. The solvent was evaporated under reduced pressure. The residue was dissolved in toluene which was then evaporated, and the same procedure was repeated. The residue obtained was chromatographed on a column of silica gel (200 g) using benzene containing 1.5% of methanol as an eluent to yield 6.4 g of the monoester product after elution of 5.0 g of the diester. Ethyl ether was added to the monoester fraction. Insoluble crystals were gathered by filtration and recrystallized from chloroform-ether to give 2.4 g of $(+)$-1(R)4(S)-4-hydroxy-2-cyclopentenyl N-mesyl-L-phenylalaninate as colorless platelets.

Yield: 19.3% m.p. 118°–119° C.

Specific rotation: $[\alpha]_D^{20} + 30.5°$ (C=2.5, CHCl$_3$)

Analysis for $C_{15}H_{19}NO_5S$ Found: C 55.50; H 5.86; N 4.22 Calculated: C 55.37; H 5.89; N 4.31

NMR spectra $\delta_{CDCl_3}^{TMS}$ 1.67 (dt, J=15.4 Hz, 1H)

2.70 (S, 3H)

2.5–3.0 (m, 1H)

3.0–3.3 (m, 2H)

4.2–4.6 (m, 1H)

4.5–5.0 )m, 1H)

3.37 (d, J=10 Hz, 1H)

5.4–5.7 (m, 1H)

5.8–6.3 (m, 2H)

7.33 (S, 5H)

IR spectra $\nu_{max}^{KBr}$ cm$^{-1}$ 3,450 3,110 1.736 1,442 1,355 1,322 1,304 1,173 1,137 1,106 1,030 753 $\nu_{max}^{CHCl_3}$ cm$^{-1}$ 1,735 1,330 1,152 1,107 977

The filtrate after filtering the above insoluble crystals was evaporated to dryness to yield 3.8 g of $(-)$-1(S)4(R)-4-hydroxy-2-cyclopentenyl N-mesyl-L-phenylalaninate as oily substance.

Yield: 30.8% Specific rotation $[\alpha]_D^{20} - 61.0$ (C=2.4, CHCl$_3$) NMR spectra $\delta_{CDCl_3}^{TMS}$ 1.67 (dt, J=15.4 Hz, 1H)

2.68 (S, 3H)

2.5–3.0 (m, 1H)

2.9–3.2 (m, 2H)

4.2–4.6 (m, 1H)

4.5–5.0 (m, 1H)

5.47 (d, J=9 Hz, 1H)

5.3–5.7 (m, 1H)

5.8–6.3 (m, 2H)

7.33 (S, 5H)

IR spectra $\nu_{max}^{cap}$ cm$^{-1}$ 3,500; 3,280; 2,940; 1,733; 1,440;

1,325; 1,157; 1,113; 1,058; 981;

757; 700;

$\nu_{max}^{CHCl_3}$ cm$^{-1}$: identical with $(+)$-compound

EXAMPLE 2

To a solution of 5.0 g of 2-cyclopentene-1,4-diol in 300 ml of methylene chloride was added 5 ml of a solution of p-toluenesulfonic acid in tetrahydrofuran (1 millimole/100 ml). A solution of 4.2 g of 2,3-dihydropyran in 30 ml of methylene chloride was then added dropwise with stirring over a period of 1 hour. After stirring overnight at room temperature, 8 drops of pyridine were added. The methylene chloride was evaporated and the residue was dissolved in diethyl ether, washed with water and dried. The residual obtained by evaporating the solvent was chromatographed on silica gel (200 g) using chloroform as an eluent. First, the diether product flowed out. The subsequent effluent was treated in a customary manner to afford 6.6 g of cis-4-tetrahydropyranyloxy 2-cyclopentenol as colorless oily substance boiling at 84° C. (0.7 mmHg).

Yield: 71.7% NMR spectra $\delta_{CDCl_3}{}^{TMS}$
1.3–2.1 (m, 7H)
2.3–3.1 (m, 1H)
3.3–4.3 (m, 2H)
4.4–4.9 (m, 3H)
6.04 (S, 2H)

IR spectra $\nu_{max}{}^{cap}$ cm$^{-1}$ 3,400 2,940 2,870 1,352 1,200 1,135

The monoether obtained above (2.8 g) was dissolved in 20 ml of pyridine, and a solution of 4.8 g of N-mesyl-L-phenylalanyl chloride in methylene chloride was added dropwise over a period of 30 minutes. The mixture was allowed to stand overnight at room temperature, and the solution was then evaporated. The residue was dissolved in ethyl acetate, washed successively with diluted hydrochloric acid, water, a diluted aqueous sodium bicarbonate solution, and then with water, dried on anhydrous sodium sulfate and evaporated. The oily residue obtained was dissolved in an acetic acid-water mixture (7:3) and allowed to stand at room temperature for 24 hours. After the reaction, the acetic acid was evaporated, and the residue was extracted with ethyl acetate and washed with alkali and acid, followed by evaporating the solvent. Ethyl ether was added to the residue to collect insoluble crystals. Recrystallization from chloroform-diethyl ether gave 1.21 g of (+)-1(R)4(S)-4-hydroxy-2-cyclopentenyl N-mesyl-L-phenylalaninate (yield 24.5%). The product thus obtained was identical with the (+)-compound obtained in Example 1.

Treating the ether-soluble fraction in a customary manner gave 2.84 g of (−)-1(S)4(R)-4-hydroxy-2-cyclopentenyl N-mesyl-L-phenylalaninate. Yield: 57.5% The product was identical with the (−)-compound obtained in Example 1.

EXAMPLE 3

The oily residue obtained by evaporating the solvent from the reaction mixture obtained by the reaction set forth in the first half of Example 2 was distilled under reduced pressure to give cis-4-tetrahydropyranyloxy-2-cyclopentenyl boiling from 103° C. to 106° C. (1 mmHg). Yield: 45%. The product had sufficient purity for use as a starting material in the following reactions.

EXAMPLE 4

Quantitative analysis by gas-liquid chromatography of the oily residue obtained by evaporating the solvent from the reaction mixture obtained by the same procedure set forth in the first half of Example 2 showed that it contained 7.6 g of the monoether compound. (Yield: 83%. The resulting oily residue (9.0 g) was treated in the same manner as described in the latter half of Example 2 using 15.7 g of N-mesyl-L-phenylalanyl chloride to give 2.9 g (yield 21.6%) of the (−)-compound and 7.1 g (yield 52.9%) of the corresponding (−)-compound.

EXAMPLE 5

To a solution of 1.5 g of cis-2-cyclopentene-1,4-diol in 100 ml of pyridine was added a solution of 3.4 g of N-tosyl-L-prolyl chloride in 30 ml of tetrahydrofuran with stirring over a period of 2 hours. The reaction was continued at room temperature for an additional 15 hours. The residue obtained after removal of the solvents was dissolved in ethyl acetate, washed and dried. The oil obtained after evaporation of ethyl acetate was distilled twice with toluene to remove pyridine, and digested in 200 ml of ethyl ether, and was then cooled.

The crystalline precipitate was removed by filtration and the filtrate was chromatographed on silica gel (80 g) using chloroform as an eluent to yield 2.6 g of a mixture of two diastereomers. Separation of the diastereomeric mixture by preparative thin-layer chromatography on silica gel afforded the following two diastereomers.

(i) 1(S)4(R)-4-hydroxy-2-cyclopentenyl N-tosyl-L-prolinate m.p. 75°–76° C.
Form: colorless needles
Specific rotation: $[\alpha]_D{}^{20}$ −167.5° (C=0.7, CHCl$_3$)
Analysis for C$_{17}$H$_{31}$NO$_5$S Found: C 58.11; H 6.02; N 3.83 Calculated: C 58.10; H 6.02; N 3.99

NMR spectra $\delta_{CDCl_3}{}^{TMS}$
1.4–2.4 (m, 5H)
2.45 (S, 3H)
2.82 (dt, J=15, 8 Hz, 1H)
3.2–3.7 (m, 2H)
4.28 (t, J=6 Hz, 1H)
4.6–5.0 (m, 1H)
5.4–5.8 (m, 1H)
5.9–6.3 (m, 2H)
7.35 (d, J=8 Hz, 2H)
7.81 (d, J=8 Hz, 2H)

IR spectra $\nu_{max}{}^{KBr}$ cm$^{-1}$
3,560; 2,970; 2,880; 1,746; 1,598;
1,337; 1,257; 1,201; 1,180; 1,158;
1,094; 1,050; 1,013; 956; 815
665; 586; 546;

$\nu_{max\ cm^{-1}}{}^{CHCl_3}$
2,970; 1,738; 1,597; 1,340; 1,157;
1,091; 1,011; 810;

(ii) 1(R)4(S)-4-hydroxy-2-cyclopentenyl N-tosyl-L-prolinate m.p. 95°–96.5° C.
Form: colorless needles
Specific rotation: $[\alpha]_D{}^{20}$ −49.1° (C=2.0, CHCl$_3$)
Analysis for C$_{17}$H$_{21}$NO$_5$S Found: C 58.31; H 5.98; N 3.87 Calculated: C 58.10; H 6.02; N 3.99

NMR spectra:
All signals were identical with those in the spectra of the 1(S)4(R) isomer except that doublet appeared at 2.82 which shifted to 2.80.

IR spectra $\nu_{max\ cm^{-1}}{}^{KBr}$
3,500; 2,970; 2,865; 1,740; 1,600;
1,342; 1,205; 1,183; 1,156; 1,094
1,050; 1,009; 956; 852; 661;
590; 543;

$\nu_{max\ cm^{-1}}{}^{CHCl_3}$
identical with the isomer

EXAMPLE 6

A mixture of 2.36 g of (−)-1(S)4(R)-4-hydroxy2-cyclopentenyl N-mesyl-L-phenylalaninate [[$\alpha$]$_D{}^{20}$ −61.0° (C=2.4, CHCl$_3$)], 3.5 g of triethyl orthoacetate, and 20 mg of hydroquinone was reacted at 155° C. for a period of 6 hours under a nitrogen atmosphere. The reaction mixture was dissolved in ethyl acetate, and washed with dilute hydrochloric acid, aqueous solution of sodium bicarbonate and then with water, followed by evaporating the solvent. The residue was dissolved in a mixture of 30 ml of methanol, 5 ml of water and 2.0 g of potassium hydroxide, and allowed to stand overnight. The acidic fraction was extracted with ethyl acetate, and dried on anhydrous sodium sulfate.

Several drops of hydrochloric acid in dioxane were added to the solution and the mixture was allowed to stand for two days. Then the solution was washed with an aqueous solution of sodium bicarbonate, and then treated in a customary manner. The oily product was purified by chromatography on silica gel (10 g) using chloroform as an eluent to yield 0.49 g of (−)-1(S)5(R)-2-oxa-bicyclo[3,3,0]oct-6-en-3-one as an oil (yield 54.4%), which was then recrystallized from n-hexane-ethyl ether mixture to give colorless needles, melting at 45°–46° C., with 100% optical purity.

Specific rotation: $[\alpha]_D^{20} - 105.1°$ (C=1.0, CH$_3$OH)
Mass spectra: M$^+$ = 124
NMR spectra $\delta_{CDCl_3}^{TMS}$
  2.2–3.1 (m, 4H), 3.3–3.8 (m, 1H)
  5.13 (dt, J=6Hz, 1H), 5.4–5.9 (m, 2H)
IR spectra $\nu_{max\ cm-1}^{KBr}$
  2,910; 1,770; 1,419; 1,348; 1,255; 1,173; 1,041; 1,010; 922; 896; 806; 723;
$\nu_{max\ cm-1}^{CHCl_3}$
  1,768; 1,346; 1,172; 1,043; 1,015; 949;

EXAMPLE 7

A mixture of 2.9 g of (+)-1(R)4(S)-4-hydroxy-2-cyclopentenyl N-mesyl-L-phenylalaninate [[α]$_D^{20}$+29.7° (C=2.0, CHCl$_3$), 4.5 g of triethyl orthoacetate, and 30 mg of hydroquinone, was reacted and treated in the same manner as described in Example 6 to give 0.58 g of (+)-1(S)5(R)-2-oxa-bicyclo[3,3,0]oct-6-en-3-one as colorless needles melting at 45.5°–46.5° C. which had 100% optical purity.

Yield: 52.5%
Specific rotation: $[\alpha]_D^{20}$+103.5° (C=1.1, CH$_3$OH)
IR, N.M.R. and mass spectra were identical with those of (−)-enantiomer obtained in Example 6.

EXAMPLE 8

(a) To a solution of 6.50 g of (+)-1(R)4(S)-4-hydroxy-2-cyclopentenyl N-mesyl-L-phenylalaninate [[α]$_D^{20}$+30.2° (C=2.1, CHCl$_3$)] and 3.36 g of dihydropyran in 250 ml of methylene chloride was added with stirring 20 ml of a tetrahydrofuran solution of p-toluenesulfonic acid (1 mmole/100 ml). After stirring the mixture for 2 hours, several drops of pyridine were added. The mixture was washed with water, dried over anhydrous sodium sulfate and evaporated to yield (+)-1(R)4(S)-4-tetrahydropyranyloxy-2-cyclopentenyl N-mesyl-L-phenylalaninate as an oily substance.

Specific rotation: $[\alpha]_D^{20}$+12.7° (C=2.6, CH$_3$OH)
IR spectra $\nu_{max\ cm-1}^{cap.}$
  3,270; 2,940; 1,735; 1,441; 1,326;
  1,155; 1,118; 1,076; 978; 916;
  866; 808; 735;
$\nu_{max}^{CHCl_3}$
  2,930; 1,735; 1,340; 1,151; 1,116;
  1,073; 1,028; 978;

(b) The oily product obtained above, without further purification, was stirred with a solution of 1.2 g of sodium hydroxide in a mixture of 30 ml of water and 80 ml of tetrahydrofuran at room temperature over a period of 5 hours. The residue resulting from the removal of tetrahydrofuran under reduced pressure was taken up in ethyl ether, washed with water and treated in a conventional manner to yield an oily product, which was then chromatographed on silica gel (80 g) using chloroform as an eluent to give 3.0 g of (−)-1(R)4(S)-4-tetrahydropyranyloxy-2-cyclopentenol.

Yield: 81.4% based on (+) monoester
Specific rotation: $[\alpha]_D^{20}$−20.3° (C=1, CHCl$_3$)

NMR spectra $\delta_{CDCl_3}^{TMS}$
  1.3–2.1 (m, 7H)
  2.3–3.1 (m, 1H)
  3.3–4.3 (m, 2H)
  4.4–4.9 (m, 3H)
  6.04 (S, 2H)
IR spectra $\nu_{max\ cm-1}^{cap.}$
  3,400; 2,940; 2,870; 1,352; 1,200;
  1,135;

(c) The monoether obtained above (1.3 g), 2.9 g of triethyl orthoacetate, and 20 mg of hydroquinone were reacted at 150° C. under a nitrogen atmosphere for a period of 12 hours. The reaction mixture was dissolved in ethylacetate, washed successively with dilute hydrochloric acid, sodium bicarbonate and then with water and treated in a conventional manner. The resulting solution was allowed to stand with a small amount of p-toluenesulfonic acid for 2 days. The mixture was washed with water, treated in an ordinary manner, and chromatographed on silica gel (30 g) using chloroform as an eluent to provide a fraction containing (−)-1(S)5(R)-2-oxa-bicyclo[3,3,0]oct-6-en-3-one. Distillation of the fraction gave 0.7 g of colorless needles melting at 45°–46° C.

Yield: 79.9%
Specific rotation: $[\alpha]_D^{20}$−104.3° (C=1.0, CH$_3$OH)
Analysis for C$_7$H$_8$O$_2$ Found: C 67.35; H 6.45 Calculated: C 67.73; H 6.50
IR, N.M.R. and mass spectra were identified with those of the product obtained in Example 6.

EXAMPLE 9

(a) in the same manner as described in Example 8 (a), 1.36 g of (−)-1(S)4(R)-4-hydroxy-2-cyclopentenyl N-mesyl-L-phenylalaninate [[α]$_D^{20}$−61.0° (C=2.4, CHCl$_3$)] was contacted with 0.7 g of dihydropyran in 40 ml of methylene chloride in the presence of 4.2 ml of p-toluenesulfonic acid as a solution of tetrahydrofuran (1 mmole/100 ml) and treated to provide (−)-1(S)4(R)-4-tetrahydropyranyloxy-2-cyclopentenyl N-mesyl-L-phenylalaninate.

Specific rotation: $[\alpha]_D^{20}$−26.8° (C=2.8, CH$_3$OH)
IR and N.M.R. spectra were identical with those of the (+)-isomer obtained in Example 8 (a).

(b) The product obtained above, without further purification, was reacted with 0.35 g of potassium hydroxide in 20 ml of methanol and treated similarly as Example 8 (b) to give 0.35 g of (+)-1(R)4(S)-4-tetrahydropyranyloxy-2-cyclopentenol as an oily substance.

Yield: 67.5% based on the starting monoester
Specific rotation: $[\alpha]_D^{20}$+21.9° (C=1.3, CHCl$_3$)
IR and N.M.R. spectra were identical with those of the (−)-isomer obtained in Example 8 (b).

(c) The monoether obtained above (1.15 g), 2.9 g of triethyl orthoacetate, and 20 mg of hydroquinone were mixed and treated in a similar manner to that described in Example 8 (c) and recrystallized from n-hexanediethylether to provide 0.56 g of (+)-1(R)5(S)-2-oxa-bicyclo[3,3,0]oct-6-en-3-one as colorless needles melting at 44.5°–46° C.

Yield: 72.2%
Specific rotation: $[\alpha]_D^{20}$+103.8° (C=1.2, CH$_3$OH)
IR and N.M.R. spectra were identical with those obtained from the (−)-isomer in Example 8 (c).

What we claim is:

1. A process for producing an optically active lactone of the following formula

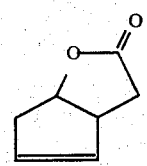

which comprises reacting a monoester of cis-cyclopentendiol of the following formula

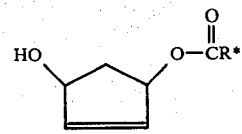

wherein

is an optically active acyl moiety, derived from an optically active neutral amino acid, the amino group of which is protected by a sulfonyl group, with a trialkyl orthoacetate, hydrolyzing the reaction product in the presence of an alkali in an aqueous solvent, and then treating the hydrolyzate with an acid to form said lactone of formula (IV).

2. The process of claim 1 wherein the monoester of formula (I) is a monoester of 1(S)4(R)-4-hydroxy-2-cyclopentenol of the following formula

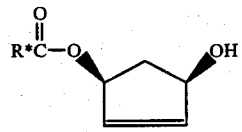

wherein

is the same as defined in claim 15, and (−)-1(S)5(R)-2-oxa-bicyclo[3,3,0]oct-6-en-3-one of the following formula

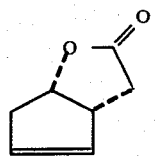

is obtained.

3. The process of claim 1 wherein the monoester of formula (I) is a monoester of 1(R)4(S)-4-hydroxy-2-cyclopentenol of the following formula

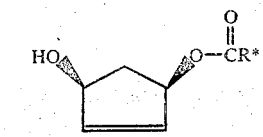

wherein

is the same as defined in claim 15, and (+)-1(R)5(S)-2-oxa-bicyclo[3,3,0]oct-6-en-3-one of the following formula

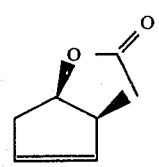

is obtained.

4. A process for producing an optically active lactone of the following formula

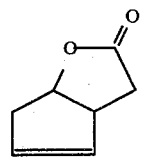

which comprises protecting the hydroxyl group of a monoester of cis-cyclopentendiol of the following formula

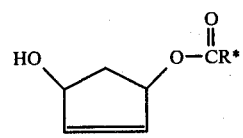

wherein

is an optically active acyl moiety derived from an optically active neutral amino acid, the amino group of which is protected by a sulfonyl group, with an acid-sensitive protective group X, hydrolyzing the protected monoester with an alkali in an aqueous solvent to form a compound of the following formula

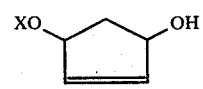

reacting the resulting compound with a trialkyl orthoacetate, and then treating the resulting product with an acid to form said lactone of formula (IV).

5. The process of claim 4 wherein the monoester of formula (I) is a monoester of 1(R)4(S)-4-hydroxy-2-cyclopentenol of the following formula

wherein

is the same as defined in claim 18, and (−)-1(S)5(R)-2-oxa-bicyclo[3,3,0]oct-6-en-3-one of the following formula (IV-2)

is obtained.

6. The process of claim 4 wherein the monoester of formula (I) is a monoester of 1(S)4(R)-4-hydroxy-2-cyclopentenol of the following formula

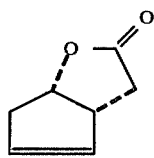 (I-2)

wherein

is the same as defined in claim 18, and (+)-1(R)5(S)-2-oxa-bicyclo[3,3,0]oct-6-en-3-one of the following formula (IV-1)

is obtained.

7. The process according to claim 4 in which the reaction product of the compound of formula (VI) with a trialkyl orthoacetate is hydrolyzed before being treated with an acid.

8. The process according to claim 1 wherein the optically active neutral amino acid is selected from the group consisting of alanine, valine, norvaline, isoleucine, leucine, norleucine, proline, phenylalanine, phenylglycine, glutamine, asparagine and methionine.

9. The process according to claim 4 wherein the protective group X is selected from the group consisting of tetrahydropyranyl, trimethylsilyl, tri-n-butyltin, and 1-methoxy-4-tetrahydropyranyl.

10. The process according to claim 4 wherein the optically active neutral amino acid is selected from the group consisting of alanine, valine, norvaline, isoleucine, leucine, norleucine, proline, phenylalanine, phenylglycine, glutamine, asparagine and methionine.

* * * * *